(12) United States Patent
Little, Jr.

(10) Patent No.: US 7,777,499 B2
(45) Date of Patent: Aug. 17, 2010

(54) HIGH-RESOLUTION, NONDESTRUCTIVE IMAGING OF DIELECTRIC MATERIALS

(76) Inventor: Jack R. Little, Jr., 912 Holystone Dr., Baton Rouge, LA (US) 70808-5108

(*) Notice: Subject to any disclaimer, the term of this patent is extended or adjusted under 35 U.S.C. 154(b) by 1042 days.

(21) Appl. No.: 11/573,020

(22) PCT Filed: Aug. 1, 2005

(86) PCT No.: PCT/US2005/026974

§ 371 (c)(1),
(2), (4) Date: Jan. 31, 2007

(87) PCT Pub. No.: WO2006/017385

PCT Pub. Date: Feb. 16, 2006

(65) Prior Publication Data

US 2009/0009191 A1 Jan. 8, 2009

Related U.S. Application Data

(60) Provisional application No. 60/598,989, filed on Aug. 5, 2004.

(51) Int. Cl.
*G01N 22/02* (2006.01)

(52) U.S. Cl. .................... 324/637; 324/631; 324/632; 324/639; 378/58; 378/62

(58) Field of Classification Search ............. 324/631, 324/632, 637, 639
See application file for complete search history.

(56) References Cited

U.S. PATENT DOCUMENTS

| 2,999,982 | A | 9/1961 | Broussaud | 324/58.5 |
| 3,025,463 | A | 3/1962 | Luoma et al. | 324/58.5 |

(Continued)

FOREIGN PATENT DOCUMENTS

JP  61274209  12/1986

(Continued)

OTHER PUBLICATIONS

Howell, C. et al., The Use of Low Cost Industrial AM-CW 'Microwave Distance Sensors' for Industrial Control Applications (no date).

(Continued)

*Primary Examiner*—Timothy J Dole
*Assistant Examiner*—John Zhu
(74) *Attorney, Agent, or Firm*—John H. Runnels; Bonnie J. Davis

(57) ABSTRACT

The enhanced detection of defects in the bulk dielectric material (Specimen) having radiation partly reflected at interfaces where the dielectric constant changes (e.g., where there are defects or structures). A sinusoidal or quasisinusoidal wave (Microwave Source) results. Localization or imaging of features is enhanced by exploiting the variation in distance resolution (Standoff+/−) in a sinusoidal or quasi-sinusoidal standing wave. At characteristic distances, the wave has a high slope and the amplitude of the wave varies strongly with small changes in distance (Standoff+/−). By inspecting at these characteristic distances (Standoff+/−), the resolution is enhanced. By systematically varying the position of the transducer or specimen, detailed images may be formed of the internal structure of the specimen across a range of depths. Defects and structures may be detected at smaller sizes than has previously been possible.

18 Claims, 4 Drawing Sheets

U.S. PATENT DOCUMENTS

| | | | |
|---|---|---|---|
| 3,144,601 A | 8/1964 | Slabodsky | 324/58.5 |
| 3,271,668 A | 9/1966 | Haake et al. | 324/58.5 |
| 3,278,841 A | 10/1966 | Hanson et al. | 324/58.5 |
| 4,087,746 A | 5/1978 | Kanae | 324/58.5 |
| 4,123,703 A | 10/1978 | Robinson | 324/58.5 |
| 4,274,288 A | 6/1981 | Tittmann et al. | 73/602 |
| 4,514,680 A | 4/1985 | Heikkila et al. | 324/58.5 |
| 4,520,308 A | 5/1985 | Rohde et al. | 324/58.5 |
| 4,581,574 A | 4/1986 | Goodman et al. | 324/58.5 |
| 4,707,652 A | 11/1987 | Lowitz | 324/58.5 |
| 5,138,255 A | 8/1992 | Kusama et al. | 324/767 |
| 5,216,372 A | 6/1993 | Zoughi et al. | 324/644 |
| 5,384,543 A | 1/1995 | Bible et al. | 324/644 |
| 5,574,379 A | 11/1996 | Darling, Jr. | 324/642 |
| 5,859,535 A * | 1/1999 | Liu | 324/632 |
| 6,172,510 B1 | 1/2001 | Liu | 324/632 |
| 6,359,446 B1 | 3/2002 | Little, Jr. | 324/637 |
| 6,480,141 B1 * | 11/2002 | Toth et al. | 342/22 |
| 6,653,847 B2 | 11/2003 | Little, Jr. | 324/637 |
| 7,190,177 B2 * | 3/2007 | Zoughi et al. | 324/642 |
| 7,456,975 B2 * | 11/2008 | De Groot | 356/497 |
| 2004/0100279 A1 | 5/2004 | Talanov et al. | 324/637 |

FOREIGN PATENT DOCUMENTS

WO     WO/9710514     3/1997

OTHER PUBLICATIONS

Kurian, J. et al., "Microwave Non-Destructive Flaw/Defect Detection System for Non-Metallic Media Supported by Microprocessor-Based Instrumentation," J. Microwave Power and Electromagnetic Energy, vol. 24, pp. 74-78 (1989).

Abu-Khousa, M. et al., "Defect Imaging and Characterization in Composite STructures Using Near-Field Microwave Nondestructive Testing Techniques," J. Composite Structures, vol. 62, pp. 255-259 (2003).

Bahr, A., Nondestructive Testing Monographs and Tracts, vol. 1: "Microwave Nondestructive Testing Methods," Gordon & Breach Science Publishers, pp. 1-85 (1982).

Bakhtiara, Sasan et al., "High-Resolution Millimeter-Wave Imaging System for Defect Characterization in Dielectric Slabs," SPIE, vol. 2275, pp. 27-33 (1994).

Bakhtiari, Sasan et al., "Microwave Noncontact Examination of Disbound and Thickness Variation in Stratified Composite Media," 8099 IEEE Transactions on Microwave Theory and Techniques, vol. 42, No. 3, pp. 389-395 (1994).

de Dieuleveult, F., "Communications au Moyen de Gunnplexer," 2198 Tote l'Electronique, No. 480, pp. 43-49 (Jan. 1983).

Ganchev, Stoyan I. et al., "Microwave Detection of Defects in Glass Reinforced Polymer Composites," SPIE, vol. 2275, pp. 11-20 (1994).

Gopalsami, N. et al., "Near-Field Millimeter-Wave Imaging of Nonmetallic Materials," $14^{th}$ World Conf. on Non Destructive Testing ($14^{th}$ WCNDT), New Delhi, India (Dec. 8-13, 1996).

Khanfar, Aws et al., "Microwave Near-Field Nondestructive Detection and Characterization of Disbonds in Concrete Structures Using Fuzzy Logic Techniques," Composite Structures, vol. 62, pp. 335-339 (2003).

Kharkovsky, S. et al., "Millimeter Wave Detection of Localized Anomalies in the Space Shuttle External Fuel Tank Insulating Foam and Acreage Heat Tiles," IMTC Conf., pp. 1527-1530 (May 2005).

Lucian, A. et al., "The Development of Microwave NDT Technology for the Inspection of Nonmetallic Materials and Composites," pp. 199-232 in Proceedings of the Sixth Symposium on Nondestructive Evaluation of Aerospace and Weapons Systems Components and Materials (San Antonio, TX 1967).

Milovanovic, B.D. et al., "Determining Mixer Diode Positions of Microwave Doppler with-Sense Module," Electronics Letters, vol. 27, No. 13, pp. 1163-1164 (1991).

Nadakuduti, J. et al., "Empirical Modeling of Surface Crack Detection in Concrete Using an Open-Ended Rectangular Waveguide," Rev. of Quant. Nondestruc. Eval., vol. 24, ed. by D.O. Thompson et al., pp. 539-546 (2005).

Qaddoumi, Nasser et al., "Microwave Imaging of Thick Composite Panels with Defects," Materials Evaluation, pp. 926-929 (Aug. 1995).

* cited by examiner

HIGH-RESOLUTION, NONDESTRUCTIVE IMAGING OF DIELECTRIC MATERIALS

The benefit of the 5 Aug. 2004 filing date of U.S. provisional patent application Ser. No. 60/598,989 is claimed under 35 U.S.C. §119(e) in the United States, and is claimed under applicable treaties and conventions in all countries.

TECHNICAL FIELD

This invention pertains to an apparatus and method for the enhanced interferometric localization of irregularities in bulk dielectric materials.

BACKGROUND ART

There is an unfilled need for improved, nondestructive means to test bulk dielectric materials for flaws, defects, irregularities, and other features; particularly to determine the three-dimensional location and profile of flaws, defects, irregularities, and other features below the accessible surface of dielectric materials. Additionally, there is an unfilled need to determine the internal, detailed structure of a specimen across a narrow range of depths. For example, there is an unfilled need for improved, nondestructive means for examining dielectric materials in three dimensions, volumetrically, and for optimizing the inspection for a selected range or ranges of depths below the surface.

An example is the unfilled need for enhanced, nondestructive means for inspecting rubber expansion joints. (This invention has numerous applications, and is not limited to the inspection of rubber expansion joints.)

Most steam-cycle electric power plants employ rubber expansion joints between the condenser and the turbine. The expansion joints have multiple composite layers. Typical dimensions for such an expansion joint are in the neighborhood of 40 meters circumference, by 25 cm wide, by 1 cm thick. Under normal operating conditions, there is a vacuum on the inside of the joint, and 1 atm pressure on the outside. Thus when such a joint fails, it is prone to catastrophic failure.

A defect can begin, for example, when a small crack allows moisture inside the rubber. Moisture can then wick along the cords that form part of the composite. The moisture can cause the cord to deteriorate, which can lead to adjacent layers delaminating from one another. Defects such as these inside a joint are difficult to detect nondestructively through conventional means.

It is highly desirable that a testing procedure be nondestructive, and be usable whether the plant is running or idle. Furthermore, because the access space outside the joint can be as little as 7-10 cm, any portion of the detection machinery that must be in contact with the joint (or in the vicinity of the joint) should be small enough to fit into such a space.

If the joint were made of metal, then well-established ultrasonic inspection techniques could be used. However, ultrasonic inspection cannot be used for rubber or soft plastic, because the polymers absorb nearly all sound energy, and reflect essentially none. The mesh or fabric of a composite material so highly scatters and disperses the ultrasonic waves that an extremely noisy reflection results. Eddy current measurements or magnetic measurements do not work well in rubber either, because rubber does not conduct electricity.

Neither is radiography particularly helpful. X-ray radiation is used to detect changes in bulk density. Under most operating conditions the most common flaw leading to failure is delamination. In a delamination failure, an essentially two-dimensional separation occurs between adjacent component layers. This separation between layers does not typically result in a detectable change in local density, and is therefore not detectable in a radiograph.

One prior method for nondestructive testing of rubber parts is to use a Durometer, a needle that penetrates a portion of the rubber, and connects to a strain gauge. Durometers have poor practical utility, but they are nevertheless commonly used in the non-destructive testing of rubber joints.

An overview of microwave testing techniques may be found in A. Bahr, *Microwave Nondestructive Testing Methods* (1982).

Several microwave nondestructive testing techniques are disclosed in A. Lucian et al., "The Development of Microwave NDT Technology for the Inspection of Nonmetallic Materials and Composites," pp. 199-232 in *Proceedings of the Sixth symposium on Nondestructive Evaluation of Aerospace and Weapons Systems Components and Materials* (San Antonio, Tex. 1967).

J. Kurian et al., "Microwave Non-Destructive Flaw/Defect Detection System for Non-Metallic Media Supported by Microprocessor-Based Instrumentation," *J. Microwave Power and Electromagnetic Energy*, vol. 24, pp. 74-78 (1989) discloses a method for detecting defects in a tire by measuring transmission of microwaves from a dipole transmitting antenna inside the tire, through the treads of the tire, with transmission detected by a linear array of detectors. Differential rates of transmission were correlated with changes in thickness or with defects.

C. Howell et al., *The Use of Low Cost Industrial AM-CW 'Microwave Distance Sensors' for Industrial Control Applications* (no date) discloses a microwave distance sensor to measure distances to an object from about 15 centimeters to about 6 meters away, by measuring the phase angle of a returned amplitude-modulated microwave signal reflected from the object.

U.S. Pat. Nos. 6,359,446 and 6,653,847 disclose an apparatus and method for the nondestructive inspection of dielectric materials. Monochromatic, phase coherent electromagnetic radiation, preferably in the 5-50 gigahertz frequency range (i.e., microwaves) impinges on the sample. In accordance with Snell's law, the microwaves are partly transmitted and partly reflected at each interface where the dielectric constant changes. A portion of the reflected beam is combined with the signal reflected by the specimen being inspected. These two signals have the same frequency, but may differ in amplitude and phase. The signals combine to produce an interference pattern, a pattern that changes as the specimen changes, or as the position of the specimen changes relative to that of the detector. In an alternative embodiment, the signal-to-noise ratio is enhanced by taking the first derivative of the Fourier transform with respect to either time or displacement.

U.S. Pat. No. 3,278,841 discloses a microwave flaw detection system, particularly for use with large, solid-propellant rocket motors. Microwaves were transmitted from inside the propellant, reflected off a metal casing, and detected by a receiver displaced from the microwave transmitter. Irregularities in the strength of the received signal were correlated with cracks or other flaws in the propellant.

U.S. Pat. No. 4,520,308 discloses a system for measuring the thickness of a dielectric material by measuring the phase shift of microwaves transmitted along a microwave strip line conductor that is adjacent to the material whose thickness is being measured. See also U.S. Pat. No. 4,123,703.

U.S. Pat. No. 2,999,982 discloses a Doppler-effect-based method for microwave detection of homogeneity defects in compact materials such as polished glass. Relatively high speeds of scanning were used to generate the desired Doppler effect. In the one example given, the relative speed of the glass versus the detector was 650 centimeters per second.

U.S. Pat. No. 3,144,601 discloses a method for microwave detection of non-homogeneous zones in non-conducting materials such as glass sheets and plates. Detection was performed by simple measurement of the echoes of the reflected microwaves; by measuring losses in intensity following transmission through the object; or by mixing incident and reflected waves to create beats, particularly when the material being examined was traveling (i.e., detecting Doppler shifts in the frequency of the reflected microwaves).

U.S. Pat. No. 3,271,668 discloses the use of microwaves to measure the rate of progressive attrition from a surface of a body of a solid dielectric material; for example, measuring the burning profile in a solid rocket motor. Microwaves were transmitted through the fuel (or other material), the surface of which reflected some of the microwaves back to a detector. The relative phase of incident and reflected microwaves varied as the distance from the microwave transmitter to the surface of the burning fuel changed, allowing the distance to the surface of the fuel to be determined as a function of time.

U.S. Pat. No. 4,707,652 discloses a technique for detecting impurities in a bulk material by measuring changes in the scattering of microwave radiation incident on the bulk material.

U.S. Pat. No. 4,514,680 discloses a method for detecting knots in lumber, by transmitting microwaves through the lumber from two sources of the same intensity, but with a 180 phase shift. Transmitted microwaves are detected on the opposite side of the lumber. If the lumber is knot-free, there is a null in the microwave field at the detectors, but if a knot is present the phase and amplitude of microwave radiation at the detectors are altered.

U.S. Pat. No. 4,581,574 discloses a method for determining the average dielectric constant of a dielectric material having a conductive surface, by transmitting microwaves from two transducers into a sheet of the material, and making measurements of the energies of reflected microwaves. By measuring average dielectric constants along a plurality of paths in the plane of the sheet, locations of variations within the sheet may be identified.

U.S. Pat. No. 4,274,288 discloses an acoustic, interferometric method for measuring the depth of a surface flaw such as a crack.

U.S. Pat. No. 4,087,746 discloses a method for determining optical anisotropy in a dielectric material by measuring changes in the polarization of microwaves transmitted through the material.

U.S. Pat. No. 6,172,510 discloses the probing of targeted portions of a layered material by microwave radiation focused onto the targeted portion by adjustment of antenna position and orientation establishing a single oblique incidence path for reflection of antenna emitted probing radiation. Signal measurements of the radiation along the oblique incidence path are obtained to provide for evaluation and detection of defects in the targeted portion of the structure being probed.

See also generally U.S. Pat. Nos. 5,574,379, 5,216,372, 3,025,463, 5,384,543; Japanese patent abstract 61274209; and published international application WO9710514.

DISCLOSURE OF INVENTION

I have discovered an improved method to enhance the detection and location of defects or other features in bulk dielectric materials. Monochromatic radiation, preferably microwave radiation, more preferably microwaves in the 5-50 gigahertz frequency range, is used to interrogate a sample. The microwaves are partly reflected at each defect or other feature where the dielectric constant changes (e.g., where there are delaminations, cracks, holes, impurities, thickness changes, other defects or structures of interest). A portion of the transmitted beam is combined with the signal reflected by the specimen being inspected. These two signals have the same frequency, but may differ in amplitude and phase. The signals combine to produce an interference pattern, a pattern that changes as the specimen changes, or as the position of the specimen changes relative to that of the detector. As illustrated in FIG. 2 (discussed in greater detail below), the interrogating radiation may be thought of as a sinusoidal (or quasi-sinusoidal) standing wave. The localization or imaging of features or irregularities is enhanced by exploiting the variation in distance resolution that results from the formation of a sinusoidal or quasi-sinusoidal standing wave. At certain characteristic distances, the standing wave has a high slope, and the amplitude of the wave varies strongly with small changes in distance. At other characteristic distances, the standing wave has a small or nearly zero slope, and the amplitude of the wave hardly varies with small changes in distance. See FIG. 2 and the discussion below. By conducting the inspection at distances where the amplitude of the standing wave varies strongly with small changes in distance, i.e., where the standing wave has a high slope, the resolution of detection or imaging is enhanced. By systematically varying the position of the transducer relative to the specimen, it is possible to create detailed images of the internal structure of the specimen across a selected range or ranges of depths. Defects and structures may be detected at smaller sizes than has previously been possible with microwave radiation. The resolution of the imaging is not limited by the wavelength of the interrogating radiation, but may be substantially smaller than that wavelength.

The detector may be scanned relative to the specimen at any desired speed, and the scanning speed need not be uniform. The novel detection technique is not based on Doppler-shifts in frequency, which result from motion, but rather is based on interference between reflected and reference microwaves that have substantially the same frequency, where the interference is caused by changes in location (independent of motion per se).

The novel technique can detect cracks, voids, foreign material inclusions (e.g., water or oil), thickness changes, delaminations, changes in dielectric constant (which in rubber may, for example, indicate aging), and other defects in essentially any dielectric materials. Different types of defects have distinguishable characteristics. The technique can also be successfully used on composite materials containing conductive components, but whose construction makes them overall nonconductors—for example, carbon fiber composites. The technique may also be used to image features that are properly part of the dielectric material, and that are not considered defects, for example the fibers in in fiber-reinforced plastic pipe, or the glass fibers in a fiberglass-reinforced polymer composite.

The novel method and apparatus have been successfully tested in a prototype embodiment. The microwave transmitter/detector was small, and readily suited for use in environments in which access space may be limited.

The signal from the detector may be plotted as "Z" in a 3-dimensional plot, where "X" and "Y" are Cartesian coordinates on the surface of a specimen under test. (Other coordinate systems may also be used in lieu of an orthogonal Cartesian system, as convenient for the shape of the particular specimen being inspected, for example cylindrical coordinates, toroidal coordinates, spherical, polar coordinates, etc.) If desired, one may determine whether a full volumetric inspection is feasible for a particular specimen with a particular transducer by placing the transducer against one surface of the specimen and moving an object on the far side of the specimen. If the microwave energy fully penetrates the specimen, the change in position of the object on the far side of the specimen should be visible in the transducer signal. Once it has been verified that the entire volume of a specimen is being adequately interrogated by the microwave beam, the scan may be optimized for maximum sensitivity at any particular depth range within the specimen by adjusting the distance between the transducer and the specimen's surface. Depending on the characteristics of a particular sample and transducer, the present invention may be used to image features to a depth of centimeters or even tens of centimeters below the surface of the sample.

The distance between the end of the transducer and the near surface of the specimen under inspection will sometimes be referred to as the "stand-off." The stand-off is illustrated, for example, in each of FIGS. 1 and 2. Changing the stand-off changes the amplitude and phase of the standing wave throughout the specimen. Changing the phase of the standing wave within the specimen changes the location of the regions of high sensitivity, $\Delta L_H$, and of low sensitivity, $\Delta L_L$, illustrated in FIG. 2. Therefore, by manipulating the stand-off distance, it is possible to optimize the detection sensitivity at a selected narrow range of depths within the specimen.

There can be ambiguity in interpreting an interferometric signal, as points within the specimen that are spaced an integral number of half-wavelengths apart may not initially be distinguished from one another, due to the identical phase of the waves reflected from such points (where the wavelength in question is that within the material, which generally differ from the wavelength in air or vacuum, depending on the index of refraction). However, if a frequency is chosen to reduce the number of wavelengths needed to traverse the thickness of the specimen, one may enhance the sensitivity at a selected depth range with minimal ambiguity. In the special case where the specimen thickness is less than (preferably substantially less than) half the wavelength, then the imaging may be optimized for a single, very narrow band of the thickness within the specimen.

Although it is preferred to inspect different depths within a specimen by varying the distance from the microwave source or transducer to the specimen, it is also possible to alter the displacement of regions of high sensitivity in the standing wave by varying the wavelength of the interrogating radiation. Accordingly, probing different depths by varying the wavelength of the radiation, instead of (or in addition to) varying the displacement of the transducer, is also considered to be within the scope of this invention.

MODES FOR CARRYING OUT THE INVENTION

Substances such as fiberglass that produce noisy reflection patterns in prior ultrasonic techniques may be inspected at low noise levels with the novel microwave technique. For example, the novel technique readily detects many common defects in fiberglass.

There are many potential fields of use for the invention. As one illustration, the invention may be used to inspect fiber-reinforced plastic (FRP) pipe. Commercially available FRP pipe is a complex composite structure, typically containing many layers of varying composition, density, and dielectric constant. When microwaves are directed towards an FRP pipe, reflections return from all interfaces between materials of different dielectric constant. The returning signal is thus a superposition of many different waveforms, essentially identical in frequency, but generally differing in phase and amplitude. In general, the full thickness of the material is inspected, and all interfaces upon which the microwaves impinge contribute to the returning waveform. The present invention provides an enhanced, unprecedented ability to "focus" on structures at a particular range of depths within a specimen, to optimize sensitivity and spatial resolution at selected depths within a specimen; or to examine the entire volume of a specimen; or both.

The novel technique relies, in part, upon the principle that a change in the reflectivity of a specimen generally indicates the presence of a flaw or other feature. Inhomogeneities act as microwave reflectors. This "different is bad" (or "different is significant") approach can be used to identify changes in thickness, foreign material inclusions, cracks, and other defects, as well as desired "features" or other components. As the location of a standing wave changes relative to a specimen, a defect may be imaged first moving into, and then moving out of the region of high sensitivity in the reflected microwave signal.

Mixing a portion of the outgoing radiation with the reflected waveform results in a complex standing waveform. (The waveform is "standing," i.e., unvarying, similar to a vibrating string, so long as the relative positions of the transducer and the specimen remain unchanged, but will generally vary as those positions vary.) As illustrated schematically in FIG. 2, the standing waveform passes from the inspection device (transducer), then usually through an intervening medium such as air, and then into the specimen. As the waveform passes through components of the specimen having differing indices of refraction, the wavelength changes, while the frequency remains constant. The higher the index of refraction, the slower the propagation of electromagnetic energy, and the shorter the wavelength becomes.

Figure 2:
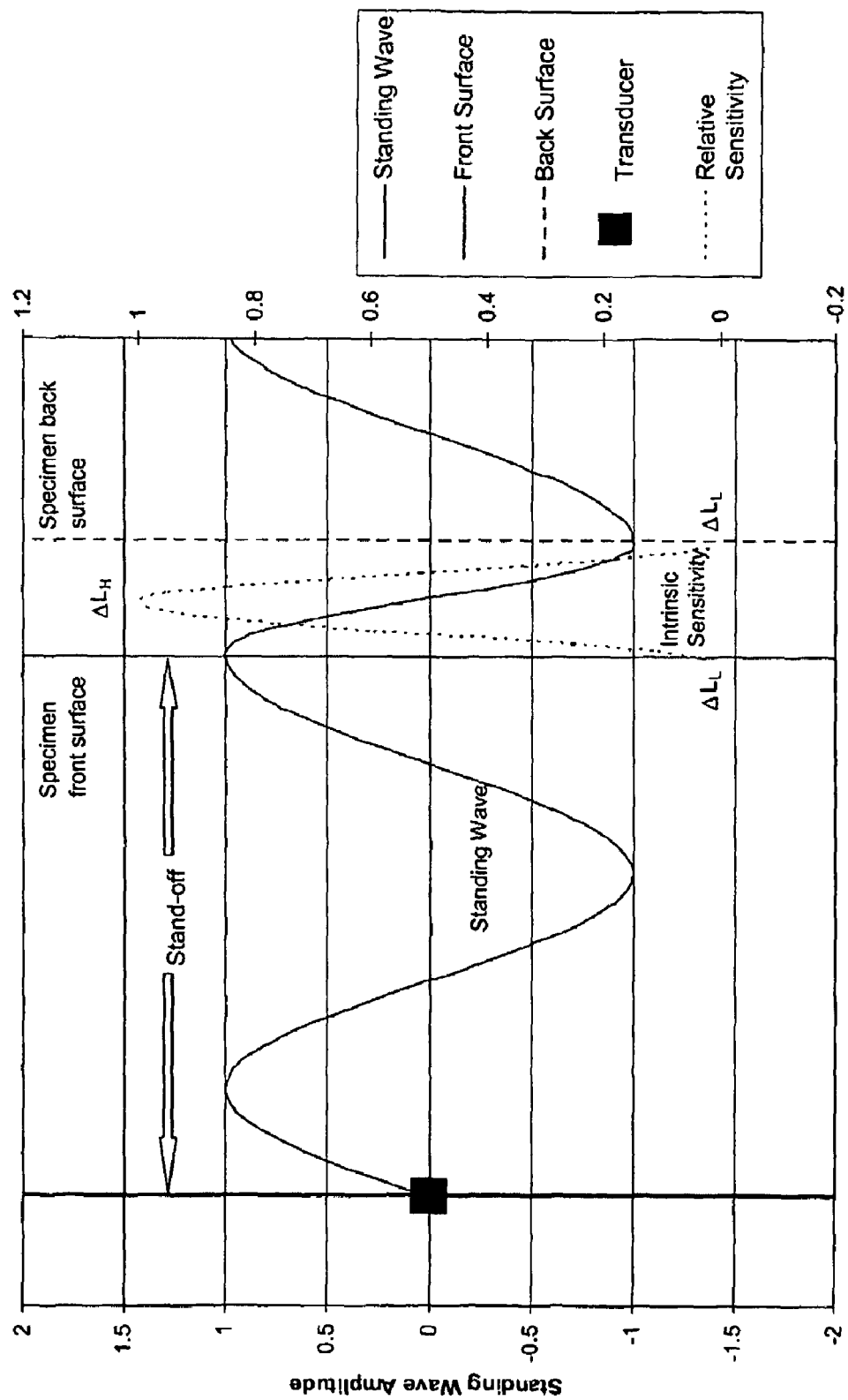
FIG. 2 depicts schematically a standing wave propagating from a transducer, through the intervening stand-off region (e.g., air), through both surfaces of a specimen, and into the space behind it.

As can be seen in FIG. 2, for a particular source-detector pair (i.e., transducer), there are regions in the waveform (shown as "$\Delta L_L$" on the sensitivity plot in FIG. 2) where a small change in the position of a defect results in almost no change in the signal reflected from the defect. These are regions in the waveform, and consequently in the material under inspection, of low sensitivity. There are also regions (shown as "$\Delta L_H$" on the sensitivity plot) where a small change in the location of a defect (or surface) results in a large change in signal. These are regions of high sensitivity. Thus the detection sensitivity depends on location. The detection sensitivity oscillates as a result of the shape of the standing wave. Quantitatively, the detection sensitivity to a small defect or structure is proportional to the absolute value of the slope of the amplitude of the standing wave at the location of the defect, as shown schematically in FIG. 2. Therefore, by altering the microwave frequency, the axial distance from the transducer to the surface, or both, any given location within the specimen may be placed into a region of high sensitivity. In general, different transducer combinations (different source-detector pairs) will be associated with standing waves having the same wavelength, but different phases.

Depending on the thickness of a particular specimen, it can be advantageous to select a combination of frequency and axial location so that only a single half-wave is present within the specimen. In such a configuration, not only may the sensitivity at any given location be maximized, but any ambiguities in location that might otherwise exist, due to multiple standing wave minima and maxima within the specimen, are simply eliminated. By scanning a sample with the detector at different distances from the surface (stand-off), it is possible to determine the range of depths of any detectable internal structure. In a preferred embodiment, each defect is imaged in the regime where the maximum amount of detail is discernable across an appropriate depth range.

To fully image the interior of a specimen, multiple depths within the specimen are thus scanned. Multiple scanning may be accomplished by multiple scans with a single transducer with a single detector, single or multiple scans with a single transducer with multiple detectors, single or multiple scans with multiple transducers with a single detector, or single or multiple scans with multiple transducers and multiple detectors. When multiple transducers are used, the various transducers may operate at the same frequency or at different frequencies. Whichever configuration is employed, it is generally preferred to use mechanical means, such as those known in the art, to adjust the stand-off from the transducer to the specimen surface. It is also generally preferred to use mechanical, electronic, or optical means, such as those known in the art, to accurately track and record the relative positions of the transducer and specimen while data are collected. The operator may place a region of interest in the specimen within a region of high sensitivity; or a portion or all of the specimen may thus be scanned, either manually or automatically.

Figure 1:
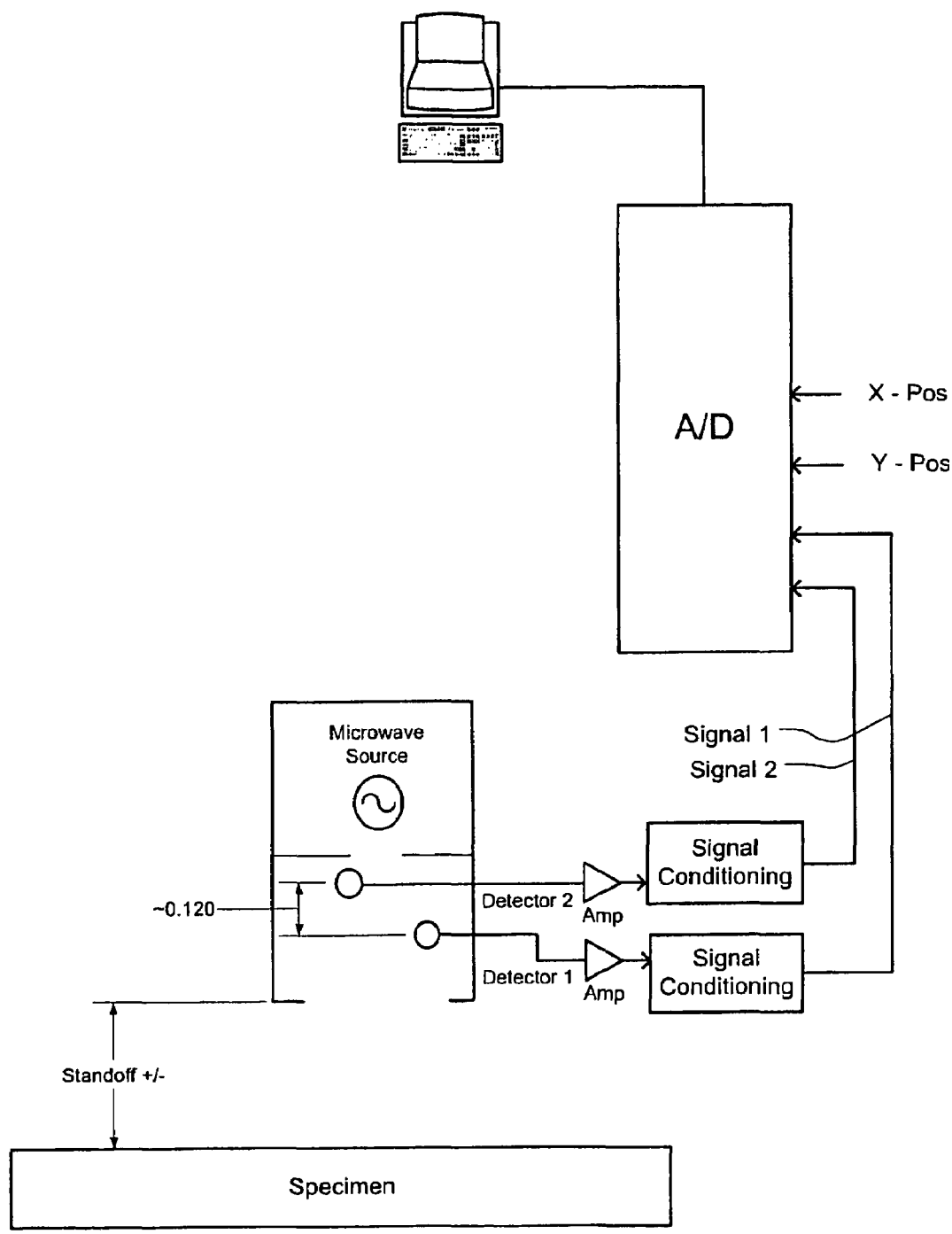
FIG. 1 depicts a schematic diagram of a prototype embodiment of an apparatus in accordance with the present invention.

FIG. 1 depicts, schematically, a prototype embodiment of an apparatus in accordance with the present invention. The prototype apparatus comprised a transducer with a single microwave source and two detectors. The detectors output two channels of SIGNAL information. The detectors were separated by approximately 0.12 inch (0.30 cm) in the direction of propagation, approximately ¼ wavelength. The transducer included mechanical means for adjusting the position and stand-off, so that any chosen region within the specimen could be examined. The SIGNALs from the two detectors were transferred to signal conditioning electronics, where they were amplified, filtered, and conditioned prior to being sent to the analog-to-digital converter (ADC). There were two position encoders, depicted in FIG. 1 as "X-Pos" and "Y-Pos," the outputs of which were also sent to the ADC. The ADC sent digital data, containing SIGNAL information for both channels, and X and Y location data, to a processing computer, which then created images for the chosen region of interest.

In the prototype apparatus, the standoff was controlled manually. In future embodiments, control of the standoff will be automated. For example, the transducer may be housed in a shaft within a hemispheric dielectric material. The standoff is controlled by moving the transducer to different positions within the shaft. The hemispheric surface allows the device to smoothly travel over uneven surfaces, while precisely controlling standoff. By automating the motion of the transducer up and down within the housing, data at different depth ranges may be acquired at rapid data transfer rates to scan specimens volumetrically rapidly or continually, manually or automatically.

FIG. 2 depicts schematically a standing wave as it propagates from the transducer, through the intervening air (standoff), through both surfaces of the specimen and into the space behind it. The index of refraction in the specimen has a value of 2.0. The sample is backed by air (index of refraction=1.0). Also depicted in the figure is a plot of the relative sensitivity at locations throughout the specimen, resulting from the particular orientation of the specimen with respect to the standing wave shown. Note that the sensitivity is the absolute value of the slope of the standing wave.

The length of a new 2" FRP pipe was inspected using the prototype device described above, with a single transducer and 2 detectors approximately 0.120" (0.30 cm) apart. The resulting image, shown in FIG. 3, clearly depicted the diagonal pattern of the internal structure of the glass rovings or fabric at the selected depth range within the pipe.

Also imaged with the prototype device was a length of 2" FRP pipe that had experienced in-service wear and failure. See FIG. 4. A breakdown in the structure of the glass fibers in the specimen was clearly visible. The normal diagonal fabric pattern was essentially absent across the selected depth range.

The Transducer

A preferred transducer was a microwave transceiver based on a Gunn diode. See, e.g., B. Hale (ed.), The 1989 *ARRL Handbook for the Radio Amateur*, pp. 32-57 & 32-58 (66th ed., 1988); *The Microwave Gunnplexer: An Introduction* (various authors, no date); M/A-COM Semiconductor Products, *Varactor Tuned Gunnplexer Transceiver "Front End"* (1985); Microwave Associates, *Varactor Tuned Gunn Oscillator Transceivers for Commercial Applications* (1977). The transducers that were used in prototype embodiments of the invention were tunable 10 or 25 gigahertz transceivers (frequencies could be higher or lower if desired, e.g., 5-50 GHz). The transceiver could be used with or without a section of waveguide. The detector had two microwave frequency diodes incorporated as part of the assembly. The detector diodes were located inside the out-going radiation beam, between the aperture and the front surface of the transducer housing. The transducer was frequency-stable, and required only a 5-10 Volt DC power supply to produce the desired microwave output energies. It was mounted in a housing, which could be moved either by hand, or in future embodiments preferably by an automated inspection device (robot).

The transducer included mechanical means to vary stand-off, so that a region of interest within the specimen could be positioned within a region of high sensitivity in the standing wave. The transducer was connected to signal processing electronics, data acquisition hardware, and an imaging and analysis computer via a multiple-conductor cable.

The transducer was also connected to a position-encoder system for determining the X and Y position of the transducer. The position encoder outputs were fed to the computer for use in imaging and analysis of the specimen.

Signal Processing and Power Supply

In the prototype embodiment, the detection diodes were located at fixed positions within the path of the outgoing microwave beam, so that the output signal maintained a constant amplitude and frequency as seen by each detection diode. Alternatively, the positions of the detection diodes could be made variable, independent of varying the stand-off distance. Microwaves radiated from the transducer to the specimen being tested. Each time the beam came to an interface between materials of different dielectric constants (e.g., the interface between the air and the specimen, or the interface between the bulk specimen and a flaw or feature within), a portion of the microwave energy was transmitted, and a portion was reflected. The portion that was reflected depended on the angle of incidence, the difference in the dielectric constants between the materials (which is related to the index of refraction), the surface texture, and other factors. Some of the reflected portion of the interrogating beam returned to the transducer, where it was detected by the detector diode. The reflected signal and the transmitted signal were of identical frequency, but (in general) differed in both amplitude and phase. These simple sinusoids or quasi-sinusoids added together (were mixed) at the detecting diode, which produced a DC voltage that changed as the sample (or portion of sample) under inspection changed. In most specimens there are many interfaces, producing many reflected signals. However, regardless of the complexity of the reflected signal, the detector diode output produced a constant DC voltage when the position of the transducer relative to the specimen and the interrogating frequency were both held constant. This constant DC voltage is sometimes referred to as the "SIGNAL." The "SIGNAL" may have multiple components, from multiple detectors.

The SIGNAL was transferred to signal processing electronics via a wired connection. The observed SIGNAL was typically on the order of 1-100 millivolts at the input of the signal processing electronics. The SIGNAL was converted from analog to digital form by the data acquisition system described earlier. The analog SIGNAL was digitized into 14 bits in the prototype, resulting in a resolution of 1 part in 16,384 (16K).

Routing the SIGNAL directly to the data acquisition system would have diminished the resolution of extremely small defects that the intrinsic frequency stability and low noise of the transducer would otherwise permit. An amplifier was therefore included in the signal processing components, prior to the ADC. The amplifier improved SIGNAL resolution by a factor greater than 100, while maintaining an acceptable signal-to-noise ratio.

The data acquisition system supported eight differentially connected analog input channels, each with its own negative signal connection. One or two analog channels were used to input amplified SIGNAL, depending on whether the transducer was equipped with one or two detector diodes. Two additional channels were used for input from the X and Y position encoders. In general, it is preferred to collect position information for both the X and Y position of the transducer. However, it sometimes suffices to collect position information from a single position encoder. For example, when collecting data for a right circular cylinder, the transducer may revolve radially around the cylinder while progressing axially down the cylinder at a known rate. Then the Y position is a direct function of the X position, and a single position encoder may suffice.

Figure 3:
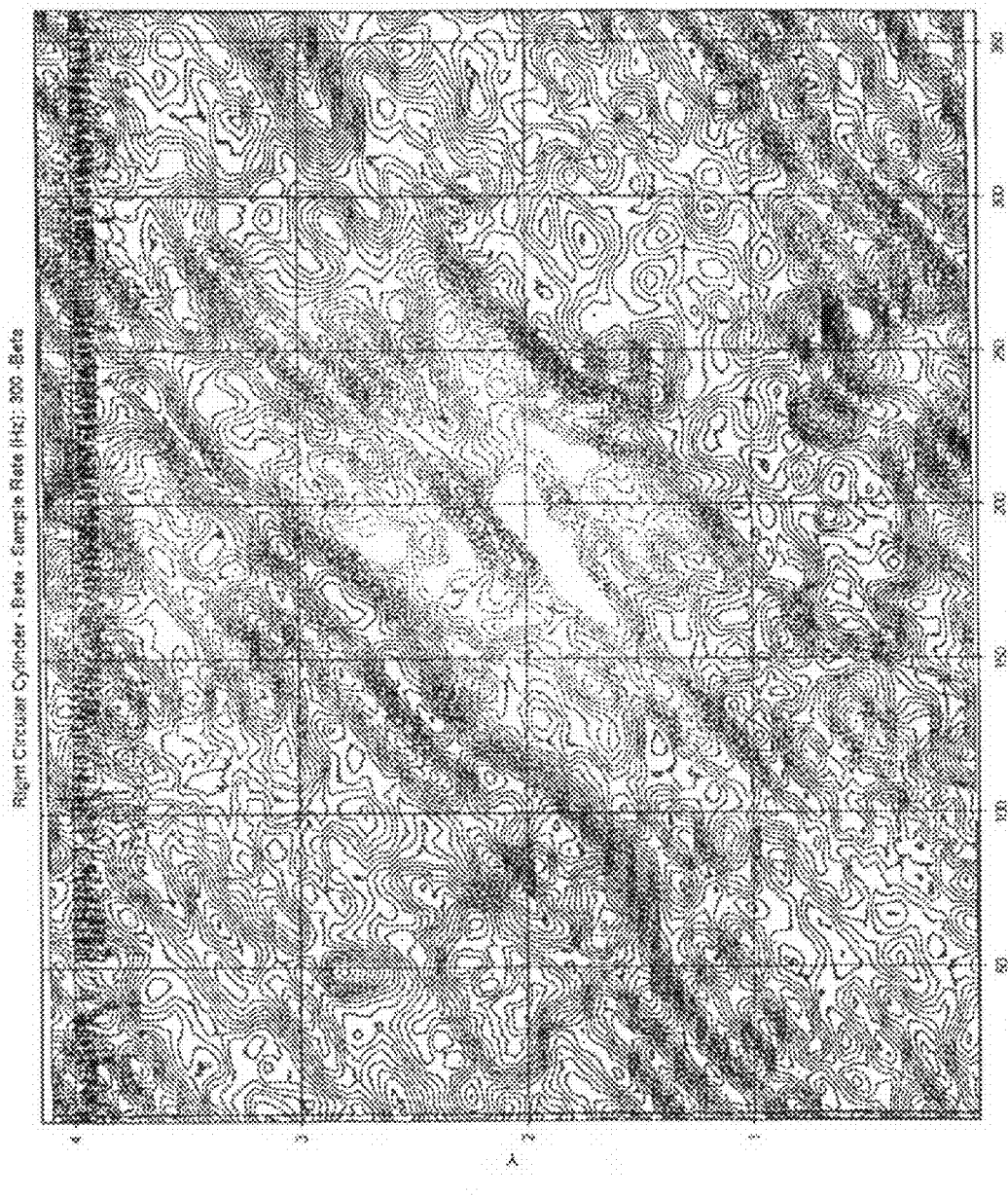
FIG. 3 depicts a contour image, made by inspection with a prototype device in accordance with the present invention, of a length of new FRP pipe without significant flaws.
Figure 4:
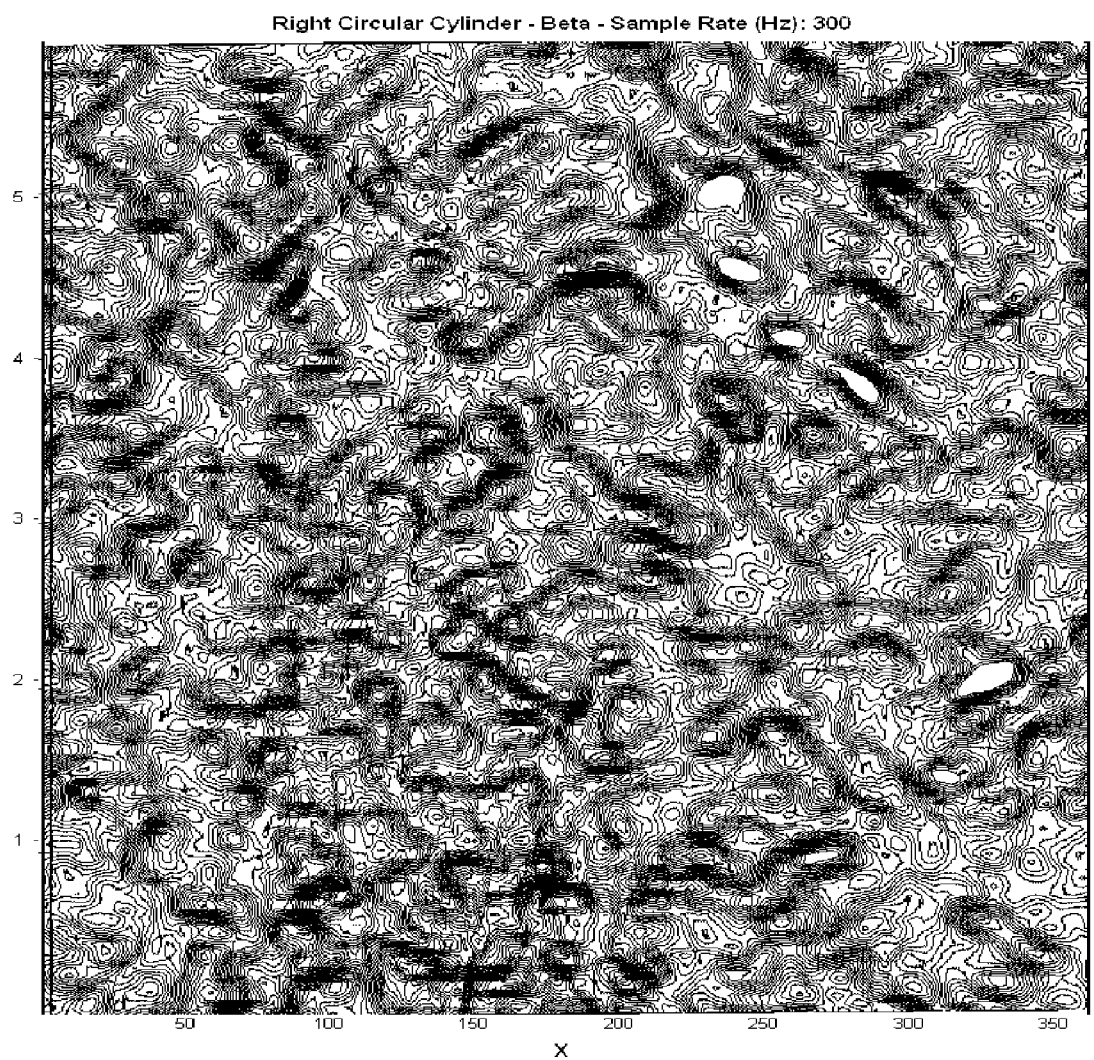
FIG. 4 depicts a contour image, made by inspection with a prototype device in accordance with the present invention, of a length of FRP pipe that had experienced in-service wear and failure.

When the data from a scan over multiple locations is displayed graphically at an appropriate scale, the resulting image shows the internal features of the specimen. Typically, the collected dataset contains far more detail than is conveniently represented in a single image. The features of interest are therefore selected, and an image is created by changing the scale and color (or gray scale) gradient for the SIGNAL for a clear visual display of the features of interest. Alternatively, as shown in FIGS. 3 and 4, contour lines may be used to display the features of interest. The stand-off spacing is selected to obtain the depth resolution desired, which is a function of the frequency of the microwaves being used, and the index of refraction of the specimen. If a transducer with multiple detectors is used (rather than a single detector), then the number of scans may be reduced, as multiple images optimized at different depths may be created with data from a single scan.

The power supply for the microwave generator comprised a regulated, low-voltage power supply between 5 and 12 VDC, capable of approximately 750 milliamps. The 5-12 volts were delivered to the transducer housing, where power was delivered to the transducer. The same power supply was configured to provide the required voltages for the amplifiers, position encoders, and data acquisition system. Power for the data acquisition system could also be provided by the notebook computer via the USB interface.

Signal Analysis, Imaging and Determination of Depth

The novel technique is based, in part, on the principle that interfaces of differing dielectric constant (defects or structures of interest) act as microwave reflectors. When a scan is made by measuring the SIGNAL at different X and Y positions, and the data are used to create an image, these interfaces can be observed, and information concerning the nature of the defect or structure may be characterized or inferred.

During scanning with the prototype device, information was simultaneously gathered for values of the two SIGNAL channels, the X location, and the Y location. These data were processed by computer to produce a two-dimensional image of the SIGNAL. When multiple scans are taken at different stand-off distances, the images differ because of the differences in sensitivity and resolution in the Z direction as a result of the sinusoidal or quasi-sinusoidal standing wave. By comparing a series of images taken at different stand-off distances—preferably, where the incremental distance between image planes is much smaller than the wavelength of the interrogating radiation—defects or structures may be detected and located at a resolution much finer than would be possible at any single stand-off. The resolution may be substantially finer than the wavelength of the interrogating radiation. This is a surprising result, as conventional wisdom would hold that it is not possible to resolve a feature whose dimensions are significantly smaller than about one wavelength.

In one approach, a marker or other defect is deliberately placed at a known depth within a test specimen. The "seeded" test specimen is then scanned to determine empirically the stand-off distances that optimize resolution of the intentionally introduced marker or defect at a particular depth. Similar tests are repeated with defects at different depths within the sample. This test information may then be used to better interpret scans of similar materials, as the relationship between optimal standoff and defect depth will already be known from the "calibration standards."

The complete disclosures of all references cited in this specification are hereby incorporated by reference. In the event of an otherwise irreconcilable conflict, however, the present specification shall control.

What is claimed:

1. A method for nondestructively detecting one or more features within a bulk dielectric material, said method comprising the steps of:
   (a) generating microwaves from a microwave source, wherein the microwaves have substantially constant frequency;
   (b) directing a first portion of the generated microwaves to the material, to create a standing wave; wherein the standing wave is a function of the wavelength of the microwaves, of the distance from the source to the material, and of the reflection of microwaves from one or more features within the bulk dielectric material, features that are characterized by at least one interface between different dielectric constants;

(c) mixing the reflected microwaves with a second portion of the generated microwaves to produce an interference pattern that is a function of the position, size, shape, and composition of the features within the bulk dielectric material;

(d) repeating steps (a), (b), and (c) with a plurality of different standing waves; wherein the standing waves differ from one another due to differing distances between the microwave source and the bulk dielectric material, or due to differing microwave frequencies, or both; and wherein the repetitions of steps (a), (b), and (c) with a plurality different standing waves may occur simultaneously, or consecutively, or both; and (e) comparing the interference patterns derived from two or more different standing waves; and inferring the position of one or more features from the locations where the interference pattern changes from one standing wave to another.

2. A method comprising repeating the steps of claim 1 for a plurality of locations within the bulk dielectric material, and forming an image that displays graphically the difference between interference patterns at the plurality of locations, whereby the image depicts features within the bulk dielectric material visually.

3. A method as recited in claim 2, wherein the image is two-dimensional.

4. A method as recited in claim 2, wherein the image is three-dimensional.

5. A method as recited in claim 1, wherein features at a selected depth range within the bulk dielectric material are preferentially detected by selecting at least some of the standing waves such that, at the selected depth range, the rate of change of the standing wave, as a function of distance from the microwave source, is at or near a local maximum, whereby changes in the interference pattern between incrementally close standing waves are enhanced for features at the selected depth range within the bulk dielectric material.

6. A method as recited in claim 5, wherein the dimensions of the features detected are substantially smaller than the wavelength of the microwaves.

7. A method as recited in claim 1, wherein the depth of a feature is determined by identifying the interference pattern having the strongest signal for the feature, and correlating the depth of the feature to the standing wave associated with the identified interference pattern.

8. A method as recited in claim 1, wherein the bulk dielectric material comprises isolated inclusions of one or more electrical conductors.

9. A method as recited in claim 1, wherein the bulk dielectric material is a composite material.

10. A method as recited in claim 1, wherein the increments between the standing waves are substantially smaller than the wavelength of the microwaves.

11. An apparatus for nondestructively detecting one or more features within a bulk dielectric material, said apparatus comprising:

(a) a generator of microwaves of substantially constant frequency; wherein said generator is adapted to direct a first portion of the generated microwaves to the material to create a standing wave; wherein the standing wave is a function of the wavelength of the microwaves, of the distance from the generator to the material, and of the reflection of microwaves from one or more features within the bulk dielectric material, features that are characterized by at least one interface between different dielectric constants;

(b) a mixer to add the reflected microwaves with a second portion of the generated microwaves to produce an interference pattern that is a function of the position, size, shape, and composition of the features within the bulk dielectric material;

(c) a computer programmed to compare the interference patterns derived from two or more different standing waves, and to infer the position of one or more features from the locations where the interference pattern changes from one standing wave to another.

12. An apparatus as recited in claim 11, wherein the computer is programmed to compare the interference patterns derived from two or more different standing waves for a plurality of locations within the bulk dielectric material, and to produce an image that displays graphically the degree of change between interference patterns at the plurality of locations, whereby the image depicts features within the bulk dielectric material visually.

13. An apparatus as recited in claim 12, wherein the image is two-dimensional.

14. An apparatus as recited in claim 12, wherein the image is three-dimensional.

15. An apparatus as recited in claim 11, said apparatus is adapted, and said computer is programmed, to preferentially image features at a selected depth range within the bulk dielectric material by selecting at least some of the standing waves such that, at the selected depth range, the rate of change of the standing wave, as a function of distance from the generator, is at or near a local maximum, whereby changes in the interference pattern between incrementally close standing waves are enhanced for features at the selected depth range within the bulk dielectric material.

16. An apparatus as recited in claim 15, wherein the apparatus is adapted to detect features that are substantially smaller than the wavelength of the microwaves.

17. An apparatus as recited in claim 11, wherein the computer is programmed to determine the depth of a feature by identifying the interference pattern having the strongest signal for the feature, and correlating the depth of the feature to the standing wave associated with the identified interference pattern.

18. An apparatus as recited in claim 11, wherein said apparatus is adapted to produce standing waves such that the increments between the standing waves are substantially smaller than the wavelength of the microwaves.

* * * * *

UNITED STATES PATENT AND TRADEMARK OFFICE
CERTIFICATE OF CORRECTION

| | | |
|---|---|---|
| PATENT NO. | : 7,777,499 B2 | Page 1 of 1 |
| APPLICATION NO. | : 11/573020 | |
| DATED | : August 17, 2010 | |
| INVENTOR(S) | : Little | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 620 days.

Signed and Sealed this

Second Day of November, 2010

David J. Kappos
*Director of the United States Patent and Trademark Office*